United States Patent [19]

Koocher et al.

[11] Patent Number: 4,727,024

[45] Date of Patent: Feb. 23, 1988

[54] BINDING ASSAYS INVOLVING FORMATION AND DETECTION OF LIGHT SCATTERING CRYSTALS

[76] Inventors: Martin Koocher, 90 Middle St., Lexington, Mass. 02173; Alan Burg, 75 Fuller Ter., West Newton, Mass. 02165

[21] Appl. No.: 862,072

[22] Filed: May 12, 1986

[51] Int. Cl.$^4$ .................. G01N 33/53; G01N 33/537; G01N 21/00; G01N 21/47

[52] U.S. Cl. ........................................ 435/7; 435/810; 436/36; 436/501; 436/518; 436/525; 436/536; 436/805; 436/808; 436/809

[58] Field of Search ................. 436/501, 805, 36, 525, 436/808, 536, 518, 809; 435/4, 7, 810

[56] References Cited

U.S. PATENT DOCUMENTS

| | | | |
|---|---|---|---|
| 3,926,564 | 12/1975 | Giaever | 436/805 X |
| 4,205,952 | 6/1980 | Cais | 436/805 X |
| 4,380,587 | 4/1983 | Koocher | 422/57 X |
| 4,480,042 | 10/1984 | Craig | 436/805 X |
| 4,565,790 | 1/1986 | Hemmila | 436/805 X |
| 4,581,337 | 4/1986 | Frey | 436/805 X |

*Primary Examiner*—Sidney Marantz
*Attorney, Agent, or Firm*—David Prashker

[57] ABSTRACT

A methodology for the detection of an analyte of interest in a fluid sample through the formation, growth, and optical detection of light scattering crystals. The methodology provides for direct assay and competitive binding assay protocols using pairs of specifically binding compositions and novel innovations in crystal growth technology to provide an analytical method which is useful in immunodiagnostic, environmental, and biochemical applications. The methodology and test kit apparatus provides rapid, reproducible, and accurate data and is sensitive for the detection of an analyte of interest present in the nanogram per milliliter range.

29 Claims, 11 Drawing Figures

BINDING ASSAYS INVOLVING FORMATION AND DETECTION OF LIGHT SCATTERING CRYSTALS

FIELD OF THE INVENTION

The invention is generally directed to improvements in heterogenous assays and is particularly concerned with qualitative and quantitative detection of an analyte of interest utilizing unique nucleation and crystal growth technology.

BACKGROUND OF THE INVENTION

Analytical assay methods, including all biochemical assays and all immunoassays, may be classified into two broad assay techniques: homogenous assays in which the reactants are combined as a reaction mixture and the process of identifying the respective end products is made without any separation of chemical components; and heterogenous assays which combine the reactants as a reaction mixture but which require a separation of the reaction products prior to their identification. Between these two broad classes, heterogenous assays have become much more commonly used for analytical research purposes and in clinical/diagnostic applications.

A particularly well known development in heterogenous assays are immunoassays which utilize the ability of specific polyclonal and monoclonal antibodies to combine selectively with antigens and haptenes. The use of such immunological components alone or in combination with other chemical compounds for qualitative and quantitative detection is now firmly established. The classical, and perhaps best known, example of a heterogenous immunoassay method is the radioimmunoassay (hereinafter "RIA") which offers established procedures for detection of a large variety of different proteins, polypeptides, hormones, drugs, and other chemical compositions. All RIA methods, regardless of individual variation, are based on the technique originally described by R. S. Yallow and S. A. Berson [*J. Clin. Invest.* 39:1157 (1960)]. Although a huge number of different variations using the basic protocol have been developed, the essence of the method relies upon a competition between an analyte of interest and its radionuclide-labeled analogue for a limited number of specific binding sites on an antibody. Under these test conditions, the concentration of the radionuclide-labeled analogue will vary inversely with the concentration of the analyte of interest in the test sample in their respective ability to bind to the specific antibody. Many variations of the competitive binding assay technique including equilibrium techniques, displacement analysis, and sequential saturation have been developed to meet a variety of different applications; a complete description of each of these different procedures is described in *Clinical Radioassay Procedures: A Compendium* (Paige K. Besch, Editor) The American Association of Clinical Chemists, Inc., 1975.

Since the essential nature of the RIA is a heterogenous assay method, it is required that a separation be made of the reaction products in order to obtain meaningful results. Accordingly, a number of different means for separating the individual chemical reaction products have been devised. In some instances, one of the reactants has been chemically bound to large, solid carriers such as red blood cells and the like which may be suspended in the reaction fluid and may be radiolabeled; in other techniques, the radiolabeled analogue or a radiolabeled antibody is immobilized onto the surface of a solid substrate. As a result, there has been a long history of developments for immobilization of a reactant directly or via the use of "linker-arms" to solids such as plastic test tubes and disks, agarose and plastic beads, porous glass, and polyacrylamide gels. [*Methods In Enzymology*, Academic Press, 1980; Updike, *Antibiotics and Chemotherapeutics* 26:67 (1979); U.S. Pat. Nos. 3,793,445; 3,970,429; and 4,138,474].

Subsequent to the development of the RIA, a wide variety of "labels" other than radionuclides, have been introduced into heterogenous assay systems for a variety of purposes. Common examples of these non-isotopic labels include fluorescent dyes, electron spin radicals, specific binding protein pairs (such as avidin and biotin), and an entire host of different enzymes used in conjunction with their respective co-factors and specific substrates. The last of these has unquestionably become the most well-known in the immunoassay art as the enzyme-linked immuno-sorbent assay or "ELISA".

Despite all these improvements in heterogenous assays, each of the presently known and used assay methodologies places undesirable restrictions and limitations on the user. For example, only the RIA technique provides an analytical sensitivity in the picogram ($10^{-12}$ gram) level while the other labeled assay techniques provide reproducible results only in the microgram ($10^{-6}$ gram) range. Unfortunately, the radionuclide label must be carefully handled and the problem of waste disposal has risen to an almost insurmountable degree. All of the presently used methods employing one of the known labels requires the use of well trained, skilled technicians and sophisticated detection equipment for accurate results. Moreover, none of the presently known methodologies are particularly useful in the field and cannot be employed on-site for either qualitative or quantitative determinations. It is apparent therefore, that in heterogenous assay methods generally and with immunoassays in particular, there remains a well recognized and continuing need for novel "labels" and new methods for detection and quantitation of an analyte.

SUMMARY OF THE INVENTION

The present invention provides a rapid, accurate and extremely sensitive method for detecting an analyte of interest in a fluid sample using direct and indirect techniques. The simplest protocol is the direct method which comprises the steps of: obtaining a conjugate reactant comprising (a) a binding partner specific for the analyte of interest, this binding partner having at least one amine group available for chemical reaction, (b) a chelatable metallic cation, and (c) a releasable marker substance having at least one carbonyl group available for chemical reaction, wherein the specific binding partner and the chelatable metallic cation agent and the marker substance have combined to form a conjugate molecule; combining the fluid sample with a conjugate reactant such that the analyte of interest binds to at least a portion of the conjugate reactant to form an analyte complexed product; separating the analyte complexed product from the unbound portion of the conjugate reactant as individual fractions; releasing the marker substance from at least one of the separated individual fractions; combining the released marker substance with an immobilized derivatizing agent such that a plurality of nucleating sites are formed in-situ, this derivatizing agent being immobilized on the surface of a solid substrate; treating the nucleating sites with a metastable supersaturated solution such that a plurality of optically detectable crystals are formed; and optically detecting the presence of the formed crystals, the presence of the crystals being a measure of the analyte of interest in the fluid sample.

The present invention also provides a preferred competitive binding assay in which a ligand analogous to the analyte of interest is employed in a competitive binding assay for qualitative and quantitative detection of the analyte of interest. In addition, a test kit apparatus is provided which maximizes the convenience and utility of the novel methodology as a whole and which permits the user to employ the assay methodology on-site in the field for a variety of different environmental, biochemical, immunological, and clinical/diagnostic applications.

BRIEF DESCRIPTION OF THE DRAWING

The present invention may be more fully and easily understood when taken in conjunction with the accompanying drawing, in which.

DETAILED DESCRIPTION OF THE PREFERRED EMBODIMENTS

The present invention is a general heterogenous assay methodology useful for detecting an analyte of interest in a fluid sample in a qualitative and/or quantitative manner. The novel methodology employs a unique identifying "label" in combination with innovations in crystal growth technology to yield accurate and reproducible results. The invention also uses the well established characteristics and utility of chemical compositions which are recognized as having the ability to specifically bind to each other and employs these chemical compositions in pairs to identify the presence and concentration of an analyte of interest. For these reasons, the applications for the present invention are not limited to immunodiagnostic assays but, instead, are generally useful in environmental studies, biochemical analysis, and general chemistry detection techniques for identification of an analyte of interest.

The unique methodology employs a variety of chemical components and reactants in a series of manipulative steps which correlate the growth of optically detectable crystals with the presence of the analyte of interest in the test sample. The preparation and use of the chemical components to identify (qualitatively and quantitatively) the presence of a particular analyte of interest in a fluid sample thus is characterized by the appearance of grown crystals observable with the unaided eye. The essential chemical components used in the present invention include the following: a conjugate reactant alternatively comprising a specific binding partner, a chelatable metallic cation, and a releasable marker substance or comprising a ligand analogous to the analyte of interest, a chelatable metallic cation, and a releasable marker substance; means for releasing the marker substance; an immobilized derivatizing agent; and a metastable supersaturated (developer) solution. The manipulative steps employing these chemical components in a direct assay procedure and in two competitive assay procedures are illutrated in schematic flow sequence by FIGS. 1, 2, and 3.

Figure 1:
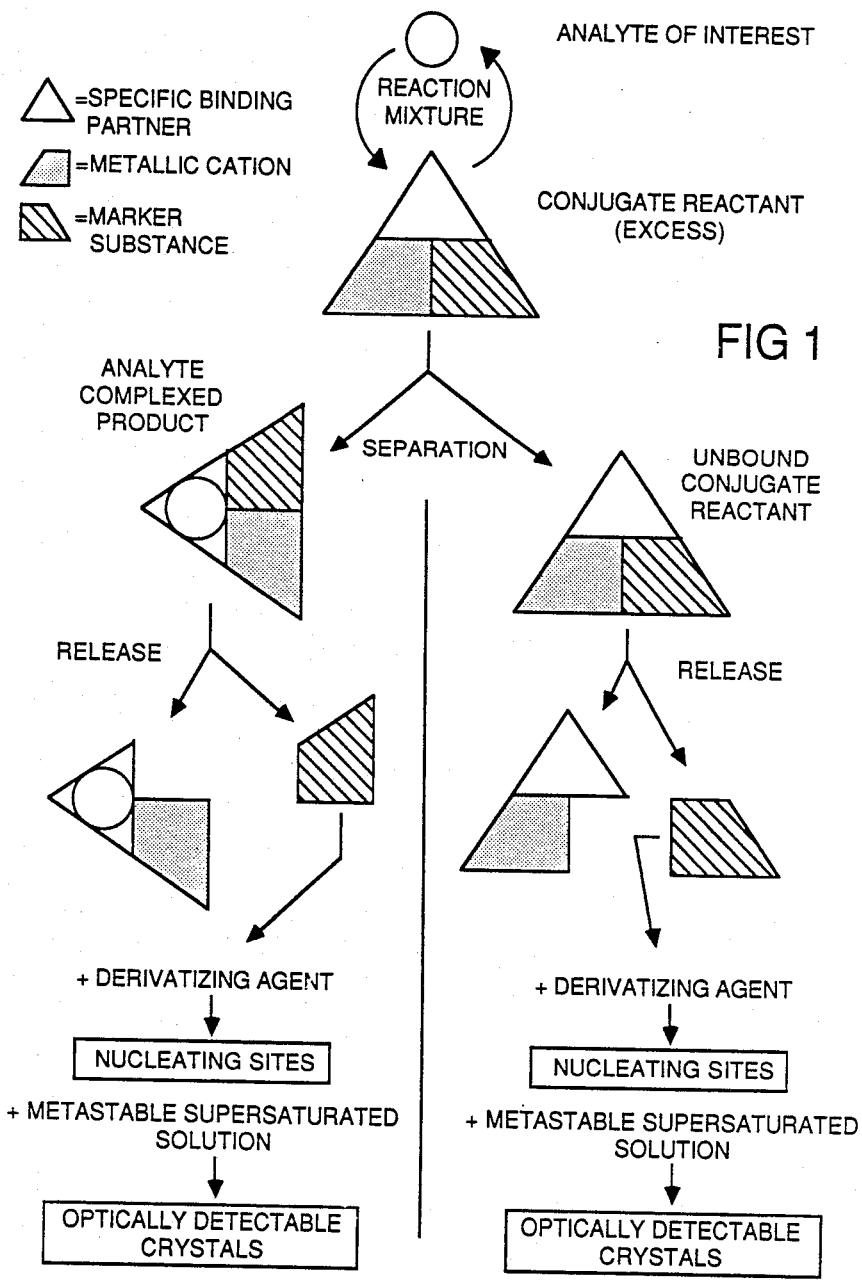
FIG. 1 is a schematic flow diagram illustrating the present invention as a direct assay protocol.

The direct assay protocol illustrated in FIG. 1 combines the analyte of interest in a fluid sample with an excess quantity of conjugate reactant comprising a specific binding partner for the analyte of interest, a metallic cation, and a releasable marker substance. The interaction between the analyte of interest and the conjugate reactant is entirely dependent upon the ability of the specific binding partner component of the conjugate reactant to specifically bind with the analyte of interest and to avoid binding with any other chemical species in the fluid. After sufficient time has elapsed for all of the analyte to combine with the excess concentration of conjugate reactant, the separation step requisite in all heterogenous assays is performed which yields separate and individual fractions: a fraction containing the analyte complexed product in which the analyte of interest has become firmly bound to the specific binding partner component of the conjugate reactant; and the fraction containing the remainder of the unbound conjugate reactant originally present in an excess but known quantity or concentration. In either instance, the sequence of manipulative steps which follows the separation of the reaction products into individual fractions is identical.

Following the illustrated sequence of manipulative steps of FIG. 1, at least one of the separated fractions is utilized and combined with specific means for releasing the marker substance, one of the components comprising the conjugate reactant. The release of this marker substance is the functional equivalent of the "identifying label" in previously known assay methods. It is the release of this marker substance and its subsequent interaction with the derivatizing agent which directly initiates nucleation and quantitatively controls the growth of optically detectable crystals comprising the remainder of the assay protocol. Accordingly, the released marker substance is placed in reactive contact with an immobilized derivatizing agent, a chemical composition which has been previously immobilized onto the surface of a solid substrate and which is able to chemically react with the marker substance to produce a plurality of fine particles in-situ, which serve as nucleating sites for crystal growth on the surface of the solid. Subsequently, a metastable supersaturated (developer) solution is added to the nucleating sites on the solid substrate. The combination of the nucleating sites and developer solution causes the formation and growth of optically detectable crystals which are visibly apparent as an opaque film. For qualitative determinations, the visual observance with the unaided eye of crystals as an opaque film identifies the presence of the analyte of interest in the fluid test sample; for quantitative assays, a determination of the total opacity will consistently provide detection of an analyte of interest in the nanogram range and, under specifically controlled conditions, detection in the picogram range.

Figure 2:
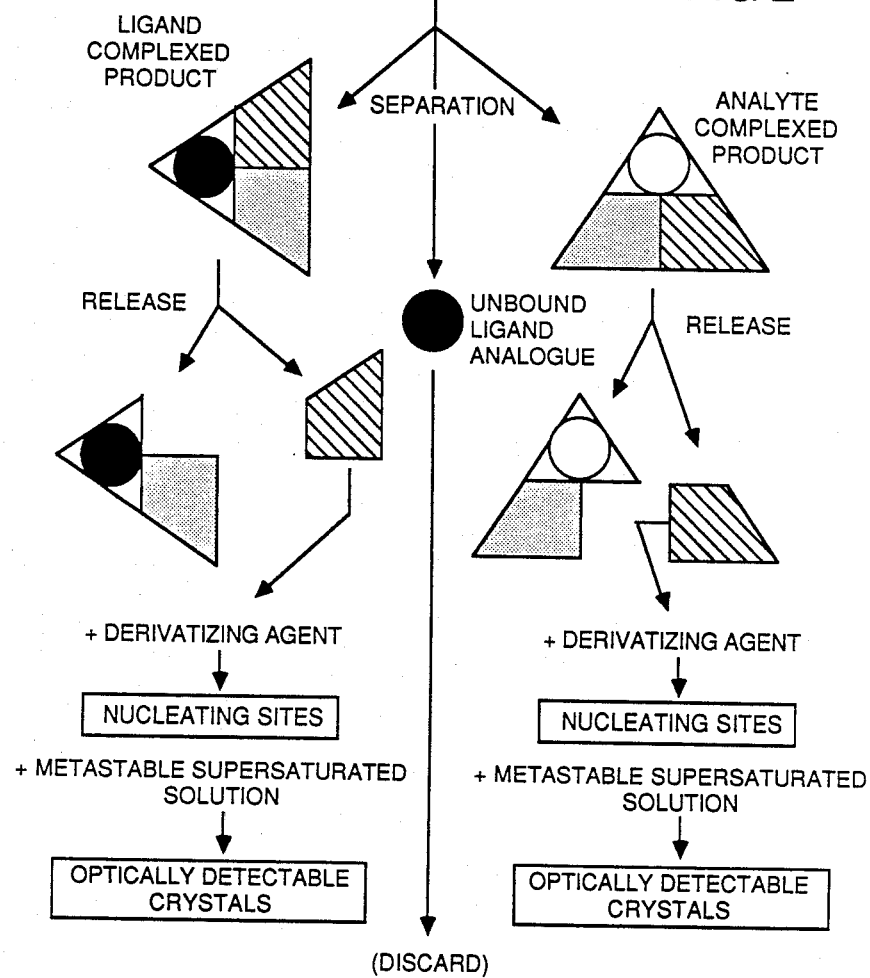
FIG. 2 is a schematic flow diagram illustrating the present invention as a competitive binding assay protocol.
Figure 3:
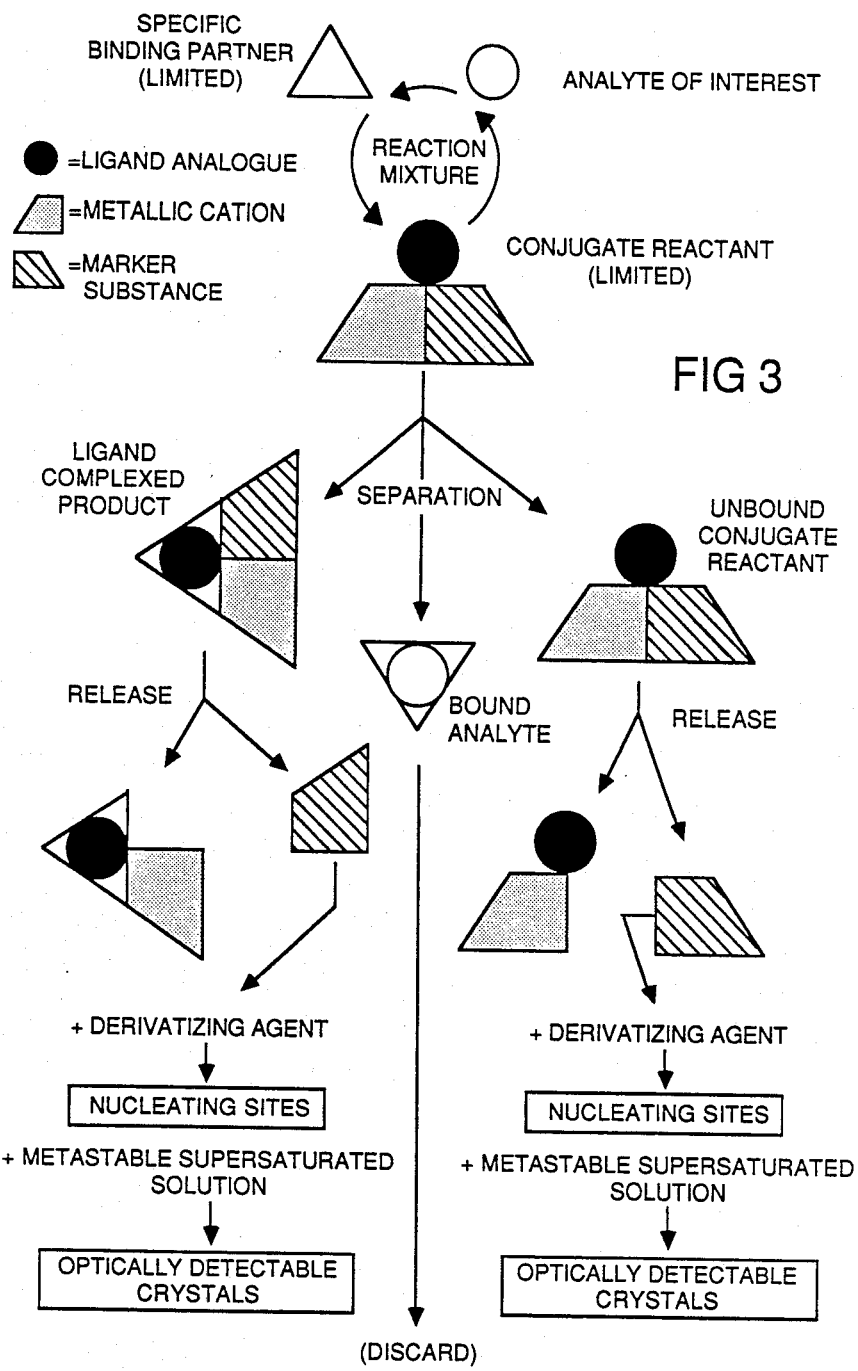
FIG. 3 is a schematic flow diagram illustrating the present invention as an alternative competitive binding assay protocol.

Preferred embodiments of the novel detection method utilizing competitive binding reactions are illustrated by FIGS. 2 and 3. The essential difference in the manipulative steps between the protocol of FIG. 2 and the protocol of FIG. 3 is the composition of the conjugate reactant which is used in limited concentration. It will be recognized that the conjugate reactant illustrated in FIG. 2 comprises a specific binding partner which is able to specifically bind to a ligand analogous to the analyte of interest as well as to specifically bind to the analyte of interest itself. This specific binding partner is combined with a chelatable metallic cation and a releasable marker substance to form a conjugated molecule. In contrast, the conjugate reactant (also in limited concentration) seen in FIG. 3 is of the alternate type and comprises a ligand analogous to the analyte of interest, a chelatable metallic cation, and a releasable marker substance. It will be understood that the chemical composition of the metallic cation and the releasable marker substance is identical in both the type 1 conjugate reactant comprising the specific binding partner and the type 2 conjugate reactant comprising the ligand analogue.

In addition, it will be observed that the competitive assay protocols illustrated in FIGS. 2 and 3 differ from the direct assay protocol of FIG. 1 in that the competitive assay protocols combine three chemical compositions as a reaction mixture either simultaneously or in addition sequence. Accordingly, in the competitive assay protocols there is a competition between the analyte of interest and the ligand analogue in the reaction mixture for the binding sites on the specific binding partner. Preferably, the quantities or concentration of conjugate reactant (both type 1 and type 2) are limited and are in optimum ratio with the limited quantity of ligand analogue such that if no analyte of interest is present in the fluid sample, the entire quantity of ligand analogue will be bound to all of the specific binding partner with little or no residual of either component; for this reason if the analyte of interest is present in the fluid sample, it will bind with the specific binding partner (present in limited concentration) and in this manner displace a specific quantity of ligand analogue which will then remain in an unbound state within the reaction mixture. This reaction sequence will occur whether or not the ligand analogue or the specific binding partner is a component of the conjugate reactant.

As seen in FIG. 2, the type 1 conjugate reactant comprising the specific binding partner is combined with the analyte of interest and the ligand analogue to form a reaction mixture in which there is competition between the analyte of interest and the ligand analogue for the binding sites of the specific binding partner component of the conjugate reactant. Because both the ligand analogue and the type 1 conjugate reactant are preferably present in limited, optimum ratio concentration, the binding of the analyte of interest with the specific binding partner will displace an equivalent amount of ligand analogue which will remain unbound and freely mobile in the fluid of the reaction mixture. After an appropriate reaction time has elapsed, each of the individual reaction products—the analyte complexed product, the ligand complexed product, and the unbound ligand analogue—are separated into individual fractions using conventional apparatus and techniques. After this requisite separation step has been performed, two of the three separated individual fractions may be utilized to obtain meaningful data: the analyte complexed product and the ligand complexed product respectively. Using either or both of these fractions, the separated complexed reaction product is combined with discrete means for releasing the marker substance. Once released, the marker substance (in vapor or fluid form) is combined with an immobilized derivatizing agent, this derivatizing agent being immobilized onto the surface of a solid substrate preferably as a film of monodispersed particles. The reaction of the marker substance with the immobilized derivatizing agent forms a plurality of nucleating sites in-situ on the surface of the solid substrate. Subsequently, a metastable supersaturated (developer) solution is added to the nucleating sites on the solid substrate which causes the formation and growth of optically detectable crystals on the surface of the solid. As is illustrated in FIG. 2, it is immaterial whether the analyte complexed product or the ligand complexed product is utilized for the formation and growth of optically detectable crystals; in either instance, the appearance of visible crystals having detectable optical properties such as opacity, will identify the presence of the analyte of interest as qualtitative and/or quantitative measurements.

The competitive reaction assay illustrated in FIG. 3 follows the sequence of manipulative steps found in FIG. 2, except that the conjugate reactant used in limited concentration is of the alternate type and comprises a ligand analogous to the analyte of interest in addition to a chelatable metallic cation and the releasable marker substance. In this protocol, the type 2 conjugate reactant is combined in sequence or simultaneously with the analyte of interest in the fluid sample and with a limited concentration of a specific binding partner (which has the demonstrated characteristic ability of binding specifically to both the analyte of interest and the ligand analogue component of the conjugate reactant). Accordingly, these are combined as a reaction mixture in which a portion of the specific binding partner binds with the analyte of interest to form a bound analyte; a portion of the specific binding partner combines with the ligand analogue of the type 2 conjugate reactant to form a ligand complexed product; and another portion of type 2 conjugate reactant remains unbound in the fluid mixture. It will be appreciated, however, that in the preferred embodiments of this protocol the quantity of specific binding partner is used in limited, optimum concentration with respect to the type 2 conjugate reactant such that if no analyte of interest is present in the reaction mixture, all of the specific binding partner will react with the type 2 conjugate reactant to form a ligand complexed product; accordingly, when the analyte of interest is present in the fluid sample, that quantity of analyte will compete with and bind to the specific binding partner thereby displacing a proportional quantity of type 2 conjugate reactant which then remains unbound in the reaction mixture. For this reason, when the reaction products are separated into individual fractions, it will be recognized that the quantity of unbound type 2 conjugate reaction and/or the quantity of ligand complexed product respectively is a measure of the quantity of bound analyte in the other fraction. On this basis therefore, either or both of these fractions may be employed in the formation and growth of optically detectable crystals.

The sequence of manipulative steps thus follows the protocol described earlier for FIGS. 1 and 2. Either or both the unbound type 2 conjugate reactant fraction and/or the ligand complexed product fraction is combined individually with specific means to release the marker substance. After the marker substance has been released, it is combined with an immobilized derivatizing agent which preferably is a monodispersed particle film on the surface of a solid substrate. The reaction of the marker substance with the immobilized derivatizing agent causes the formation of a plurality of nucleating sites on the surface of the solid. Subsequently, a metastable supersaturated (developer) solution is added to the nucleating sites to cause formation and growth of optically detectable crystals on the surface of the solid. The grown crystals are visually apparent with the unaided eye and may be optically determined for specific characteristics such as diffuse reflectance and opacity. In this manner, the presence of optically detectable crystals provides both qualitative and/or quantitative data for the analyte of interest in the fluid sample.

It will be appreciated that in all embodiments of the present invention, means for separating the individual reaction products must be employed regardless of the specific manner in which the methodology is performed. The means and apparatus for separating the reaction products into individual fractions are those conventionally known and available in the art, many of which are commercially sold. In the preferred embodiments of the present invention, separation into individual fractions is achieved by methods including filtration, decantation, centrifugation, and use of solid phase substrates to immobilize one or more chemical components. For example, in instances where insoluble carriers (such as red blood cells, white blood cells, specific tissues and the like) are utilized to support or present the analyte of interest on their surfaces, these insoluble carriers may be separated from the reaction mixture by sedimentation, filtration, and decantation. The use of such naturally occuring carriers (blood cells and the like) also allows the user to perform the assay in a direct mode as is illustrated in FIG. 1. Alternatively, when performing competitive reaction assays, it is preferred that the ligand analogue or the specific binding partner be immobilized directly or through the use of extended "linker-arms" to the surface of a solid substrate; methods for immobilizing the specific binding partner and the ligand analogues are conventionally known in the art and are available in a variety of different reactions to meet the specific needs of individual compositions. Among the solid substrates which are useful for immobilization are insoluble polymers or plastics including latex beads, bentonite particles, cellulose, cross-linked dextrans, and beads of agarose and polyacrylamides. Fluid soluble ligand analogues and specific binding partners are directly attached to these solid substrates via specific chemical reactions well established and described in the art. Accordingly, the means for immobilizing and separating the reaction products are deemed to be insignificant with respect to the present invention as a whole and are neither limiting nor restrictive of the applications and the manner in which the present invention is performed as a series of manipulative steps.

The advantages provided by the present invention are both substantial and multiple: the method for detecting an analyte of interest in a fluid sample is rapidly performed and efficient in its requirements of test sample size and volume of reactants; the methodology, regardless of whether it is performed in a direct or indirect competitive mode, provides accurate and reproducible data; the present methodology provides the user with a choice of qualitative and/or quantitative results to meet his specific needs or desires; the test results are visually observable to the naked eye and are verifiable using unsophisticated detection equipment; the unique methodology does not require great knowledge or information on the part of the user to obtain accurate results and does not require the user to be highly skilled or technically trained; the apparatus for performing the novel protocols is presently available in the art and is relatively inexpensive to obtain; the method may be performed accurately and reproducibly in the field thereby eliminating any need to prepare and/or deliver specific samples to a specific location and thus avoiding the inherent problems of stability of sample, transportation, and storage associated with the transfer of specimens; finally, the sensitivity of the present methodology provides reproducible results consistently in the nanogram per ml range.

To fully appreciate the broad range of applications and uses with which the present invention may be employed, a detailed description of the variety of analytes which may be detected and the various chemical components used in the manipulative steps comprising the methodology will now be presented. It is expressly intended and explicity understood, however, that the chemical composition and formulations for each described component are merely exemplary of the range of compositions which may be used and are illustrative of the purposes and goals which may be achieved. In no respect, are the described embodiments to be deemed restrictive or limiting of the invention as a whole.

The Analyte of Interest

The analyte of interest is that chemical species to be detected in a fluid test sample using the manipulative steps comprising the present methodology. There is one, and only one essential requirement: the existence of a discrete binding partner which is specific for and will selectively bind to the analyte of interest in a fluid medium. It is immaterial whether the analyte of interest is soluble or insoluble in the fluid medium or whether the analyte of interest is a chemical moiety comprising part of a larger molecule so long as the analyte is to be found on the surface of the molecule and is available for chemical reaction. The existence of such pairs of specifically binding chemical compositions is well established and includes the following: polyclonal and monoclonal antibodies, Fab fragments, Fab' fragments and their respective antigens and/or haptenes; specific binding pairs such as avidin and biotin; hormones and their respective receptor sites; enzymes and their respective specific co-factors and inhibitors; and specific metallic ions and chelating agents. The true chemical composition and/or formulation of the analyte of interest is inconsequential and not significant. Accordingly, the analyte may comprise: proteins, polypeptides, lipoproteins, amino acids, ionizable metals and salts, enzymatic co-factors and substrates, and the like. In the preferred immunodiagnostic applications, it is expected that antibodies and antigens (or haptens) and any of their respective derivatives regardless of source will be most commonly used, the degree of specificity and affinity of the antigen for its specific binding partner being empirically demonstratable via the wide variety of known techniques now available.

The Ligand Analogous To the Analyte of Interest

The ligand analogue is a chemical composition identical or similar to the analyte of interest. It is chosen on the basis of its ability to also selectively bind with the binding partner specific for the analyte of interest. The ligand analogue is useful in those competitive binding assays illustrated by FIGS. 2 and 3. The ligand analogue is added to the reaction mixture at a limited concentration for optimal binding with the specific binding partner and will be displaced and prevented from binding by such analyte of interest as is present in the fluid sample. In most instances, it is intended and expected that the chemical composition and formulation of the ligand analogue will be identical to that of the analyte of interest; in a limited number of cases however, the ligand analogue will be of different chemical composition but will demonstrate a selective binding capacity for the specific binding partner which is similar or identical to the binding capacity of the analyte of interest.

It will be recognized that the ligand analogue may be employed in two different modes: as a discrete entity and competitor for the analyte of interest for binding to the specific sites of the binding partner; and as one component comprising the type 2 conjugate reactant. In the competitive binding mode, the discrete ligand analogue is typically immobilized onto the surface of a solid substrate prior to use using methods and reagents conventionally known in the art. The immobilization of the discrete ligand analogue thus provides the means for separating the reaction products after the competitive binding reaction has proceeded to equilibrium. In the second mode, as one of three components comprising the type 2 conjugate reactant, it is required that the ligand analog have at least one primary amine group available for chemical reaction. In those instances where the ligand analogue chosen does not contain at least one amine group in its natural state or formulation, it is required that the ligand analogue be reacted with an amine containing compound to form a hybrid reaction product. It is essential also that this hybrid reaction product retain the selective binding capacity for the specific binding partner previously demonstrated. It must be understood and emphasized, however, that this additional procedure of adding at least one amine group to the functional ligand analogue is necessary only in those instances where the conjugate reagent is to be prepared and only in those instances where there is no amine group available in the ligand analogue molecule initially.

The Specific Binding Partner

The specific binding partner, as illustrated in FIGS. 1-3, has only one essential function and only one requisite feature: a demonstrable ability to selectively bind with the analyte of interest and the ligand analogue. In those instances where the analyte of interest and the ligand analogue are identical, the binding capacity, the optimum binding ratios, and the strength of the bond at each of the binding sites or receptors will be identical; in other instances, however, where the analyte of interest and the ligand analogue are not chemically identical, it is necessary that the degree of affinity and strength of binding for the specific partner to the ligand analogue be similar in degree, nature of bond, and strength of bond to that present in reactions with the analyte of interest.

The specific binding partner may be employed in one of two modes: in the first mode, the specific binding partner is used as a discrete entity in the competitive binding assay protocols in limited concentration such that if no analyte of interest is present within the fluid reaction mixture, all of the ligand analogue will bind with that quantity of specific binding partner present in the fluid. In this competitive binding mode, the chemical composition, formulation, or specific structural orientation of the specific binding partner is immaterial so long as the demonstrated selective binding capacity is retained. Although the specific binding partner will be a protein or polypeptide in a majority of instances and may functionally be classified as an antibody (of monoclonal or polyclonal origin), or an antibody fragment (such as a Fab fragment or Fab' fragment) this is not an essential feature or requisite limitation. For example, a specific binding partner may be a polysaccharide inhibitor which is specific for an enzymatic analyte of interest. It is also expected and intended that in some competitive binding assays the specific binding partner will be immobilized onto the surface of a solid which will then provide the means for separating the chemical entities in the reaction mixture. It is again emphasized that the means for immobilizing any specific binding partner employ those reactions and chemistries well established and known in the prior art; accordingly the fact that the specific binding partner is employed in an immobilized state or in a freely mobile state is insignificant with respect to the present invention.

The second mode of employing the specific binding partner is as one component comprising the type 1 conjugate reactant. When used in this mode, there is a second essential requirement imposed for the chosen specific binding partner: the presence of at least one primary amine group for chemical reaction as part of the overall chemical composition. In those instances where the specific binding partner is composed of nitrogen containing constituents such as amino acids, primary and the like, this requirement is naturally satisfied. In those instances where the specific binding partner does not contain at least one amine group available for subsequent chemical reaction, it is necessary to combine this chosen specific binding partner with an amine containing composition to form a hybrid reaction product using reagents and reactions conventionally available in the art. In this manner, the hybrid reaction product will be utilized as the functional equivalent of the specific binding partner and will demonstrate both essential requirements: the ability to selectively combine with the analyte of interest; and the availability of at least one amine group for chemical reaction. It is again noted, however, that this latter requirement and the alternative procedure for making a hybrid reaction product is necessary and useful only in those instances where the specific binding partner is to be employed as one component in preparing the type 1 conjugate reactant.

The Conjugate Reactant

As is illustrated by FIGS. 1-3, the conjugate reactant in this novel detection methodology serves as the functional equivalent of the "identifying label" commonly found in prior art assay techniques. Within the present invention, however, the conjugate reactant is prepared in alternative forms which utilize either the specific binding partner or the ligand analogue as a component.

The conjugate reactant identified herein as type 1 employs the specific binding partner as a component in combination with a chelatable metallic cation and a releasable marker substance. Alternatively, the conjugate reactant identified herein as type 2 employs the ligand analogue as a component in combination with a chelatable metallic cation and a releasable marker substance.

The chemical relationship and manner of preparing the conjugate reactant is identical without regard to whether the type 1 or type 2 composition is made. The choice of metallic cation and of releasable marker substance may be identical in both the type 1 and the type 2 forms; alternatively, the chosen metallic cation and the chosen releasable marker substance may be varied as desired when preparing the alternate forms. It will be expressly understood however, that there is no meaningful difference between the type 1 and the type 2 conjugate reactant forms with respect to the chelatable metallic cation and the releasable marker substance; the only recognizable and meaningful difference, therefore, is solely with regard to the use of either the specific binding partner or the ligand analogue as a component.

Regardless of its exact chemical composition, its structural orientation, or its specific activity, the conjugate reactant is a stabilized imine complex, or in alternate terminology, a stabilized Schiff base. The stabilization of the conjugate reactant is provided by the chelatable metallic cation which, in turn, also offers the specific means for releasing the marker substance from the complex on demand in a controlled manner. The releasable marker substance in each instance contains at least one carbonyl group

group available for chemical reaction. Accordingly, when the specific binding partner or ligand analogue having the requisite amine group is combined with the releasable marker substance having the requisite carbonyl group and the metallic cation, a stabilized imine complex (or stabilized Schiff base) is formed. The general reaction sequence is represented by Synthesis I below:

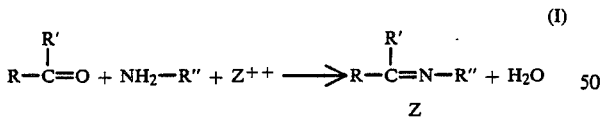

wherein R, R', and R" are selected from the group consisting of alkyl, aryl, aromatic and aliphatic compounds and hydrogen.

In many instances, it is expected that the specific binding partner or the ligand analogue used in preparing the conjugate reactant will have a plurality of other reactive groups and that the chosen releasable marker substance will also provide reactive groups in addition to the requisite carbonyl group. These instances are exemplified by the presence of the alpha amino acid lysine within a polypeptide chain. the lysine having a second amina group on the epsilon carbon atom available for reaction; a preferred aromatic substance, salicylaldehyde; and a preferred chelatable metallic cation, cupric copper. These reactants combine to form a stabilized Schiff base. The most likely configuration of this stabilized imine complex is controlled by the releasable marker substance, an aldehyde capable of pi-bond activation such as salicylaldehyde, in combination with the ability of the metallic cation to stabilize the Schiff base once formed. The overall reaction sequence is is given by Synthesis II.

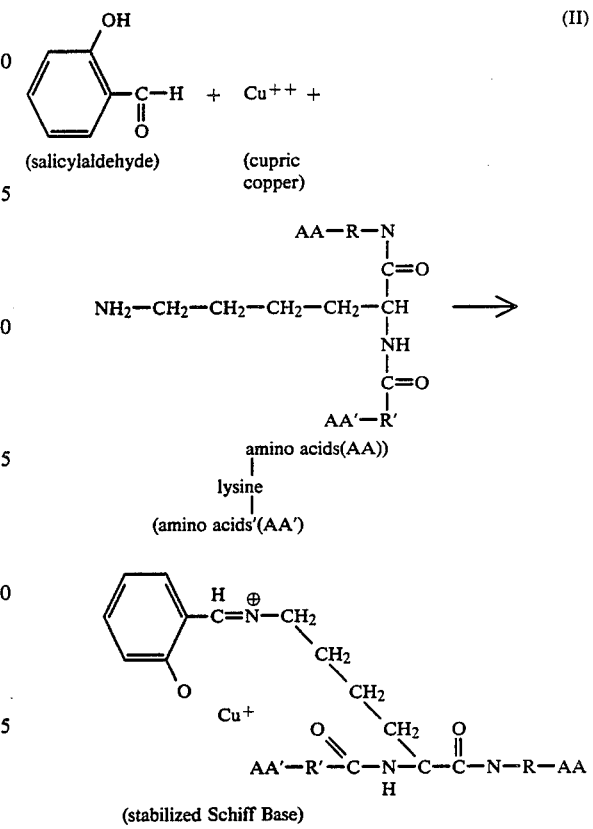

The stabilization of a Schiff base through the incorporation of a metallic cation is well described and documented in the literature [Eichhorn and Marchaud, J. Am. Chem. Soc. 78:2688-2691 (1956); Gunther et al., J. Am. Chem. Soc. 78:2688-2691 (1956); Nunez et al., J. Am. Chem. Soc. 84:901-906 (1962); Bai et al., J. Am. Chem. Soc. 89:6126-6130 (1967)]. The existence of such stabilized imine complexes and the methods for preparing stabilized Schiff bases are thus well established reactions available in the art; nevertheless, the manner of releasing the carbonyl-containing marker substance, its functional value and utility as a releasable component, and the range of compositions useful within stabilized imine complexes is neither appreciated nor recognized in the existing literature. For these reasons, each of the components comprising the conjugate reactant as employed in the present invention will now be described in detail.

The Specific Binding Partner and Ligand Analogue

The chemical nature, function, and specific activity of both the specific binding partner and ligand analogue have been described herein previously. As a component in the conjugate reaction, only two features are essential and required: the demonstrable ability to selectively bind with another entity as a specific binding pair; and the availability of at least one amine group for chemical reaction with the carbonyl group of the releasable marker substance in the presence of a chelatable metallic cation to form a stabilized imine complex. The most common examples are proteins and polypeptides which have the demonstrated ability to bind selectively. As noted previously, a hybrid reaction product may also be made which will functionally and chemically provide both requisite elements.

The Chelatable Metallic Cations

The preferred chelatable metallic cations are the ionizable metals such as cupric copper [$Cu^{++}$], nickel [$Ni^{++}$], and zinc [$Zn^{++}$]. These metal ions provide the required degree of stability in the conjugate reactant and yet allow the marker substance to be chemically or physically releasable in subsequent manipulative steps. Other metallic cations which may also be employed include ferric iron [$Fe^{+++}$], cadmium [$Cd^{++}$], and cobalt [$Co^{++}$]. In general, any chelatable ion is deemed useful. The choice and concentration of metallic cation typically will vary with the chemical composition of the other components selected, their concentration, and the pH of the reaction medium.

The Releasable Marker Substance

The preferred marker substance must satisfy at least two, and preferably three, requirements: it is essential that the marker substance have at least one carbonyl group available for reaction with the specific binding partner or ligand analogue in order to form a stabilized imine complex. It is desirable that the strength of the stabilized imine bond of the complex be sufficiently strong and endurable to maintain the chemical integrity of the conjugate reactant as a whole for use in the methodology; and subsequently that this imine bond be easily destabilized and cleaved by physical or chemical means for quick release of the marker substance from the conjugate reactant on demand. It is also essential that the released marker substance then be able to chemically react with an immobilized derivativizing agent to form a series of nucleating sites in-situ for the growth of crystals.

The first of these requirements, the presence of at least one carbonyl group has been previously described in detail. The range of chemical compositions having such a carbonyl group is extensive and includes many different classes and varieties of chemical compositions including alkyl, aryl, aliphatic and aromatic compositions which may or may not include additional functional reactive groups. It is recognized, that those carbonyl compositions having a lesser rather than a greater molecular weight and those having a simplified three dimensional structure rather than a more complex structure are preferred for their ease of use and preparation; nevertheless, neither the true molecular weight, structural orientation, complexity, or other chemical and functional characteristics of the chosen composition are significant so long as these do not substantially interfere with the purposes of the marker substance in the preparation of the conjugate reactant and the use of the stabilized imine complex in the methodology comprising the present invention. Exemplifying without limitation the variety of different chemical compositions having at least one carbonyl group for reaction which are deemed useful as releasable marker substances are those listed in Table I:

TABLE I

| Releasable Marker Substance | Preferred Derivatizing Agent | Preferred Metastable Supersaturated (Developer) Solution |
|---|---|---|
| Salicylaldehyde | p-Hydroxybenzoic Acid Hydrazide | Salicylaldehyde-p-Hydroxybenzoic Acid Hydrazone |
| 4-Chloro-salicylaldehyde | p-Hydroxybenzoic Acid Hydrazide | 4-Chloro-salicylaldehyde-p-Hydroxybenzoic Acid Hydrazone (Salicylaldehyde-p-Hydroxybenzoic Acid Hydrazone)* |
| 5-Chloro-salicylaldehyde | p-Hydroxybenzoic Acid Hydrazide | 5-Chloro-salicylaldehyde-p-Hydroxybenzoic Acid Hydrazone |
| 4,6-Dimethyl-salicylaldehyde | Salicylhydrazide | 4,6-Dimethyl-salicylaldehyde Salicylhydrazone |
| 3-Ethoxy-salicylaldehyde | Salicylhydrazide | 3-Ethoxy-salicylaldehyde Salicylhydrazone |
| 3-Fluoro-salicylaldehyde | Salicylhydrazide | 3-Fluoro-salicylaldehyde Salicylhydrazone |
| 4-Methoxy-salicylaldehyde | Nicotinic Acid Hydrazide | 4-Methoxy-salicylaldehyde Nicotinic Acid Hydrazone |
| 5-Methyl-salicylaldehyde | Nicotinic Acid Hydrazide | 5-Methyl-salicylaldehyde Nicotinic Acid Hydrazone |
| 5-Sulfo-salicylaldehyde | Nicotinic Acid Hydrazide | 5-Sulfo-salicylaldehyde Nicotinic Acid Hydrazone |
| 2-Hydroxy-1-naphthaldehyde | 2,4-Dinitrophenyl Hydrazine | 2-Hydroxy-1-naphthaldehyde 2,4-Dinitrophenyl Hydrazone |
| 2-Hydroxy-3-naphthaldehyde | 2,4-Dinitrophenyl Hydrazine | 2-Hydroxy-3-naphthaldehyde 2,4-Dinitrophenyl Hydrazone |
| 2-Hydroxy Cinnamaldehyde | p-Carboxyphenyl Hydrazine | 2-Hydroxy Cinnemaldehyde-p-Carboxyphenyl Hydrazone |
| Pyridoxal | p-Carboxyphenyl Hydrazine | Pyridoxal-p-Carboxyphenyl Hydrazone |
| 2-Thiophene Aldehyde | p-Carboxyphenyl Hydrazine | 2-Thiophene-aldehyde-p-Carboxyphenyl Hydrazone |
| Pyrrolaldehyde | Semicarbazide | Pyrrolaldehyde-Semicarbazone |
| 4-Hydroxynicotinaldehyde | Semicarbazide | 4-Hydroxynicotinaldehyde Semicarbazone |
| 3-Hydroxy Isonicotinaldehyde | Semicarbazide | 3-Hydroxy Isonicotinaldehyde-Semicarbazone |

*Since Salicylaldehyde-p-hydroxybenzoic Acid Hydrazone is isomorphic with 4-Chloro-salicylaldehyde p-Hydroxy Benzoic Acid Hydrazone, it can be used as the metastable supersaturated (developer) reagent to visualize 4-Chloro-salicylaldehyde p-Hydroxy Benzoic Acid Hydrazone nuclei. Proper choice of reagent solvent is very important in this case. When this phenomenon is exploited, it is referred to as epitaxy.

As will be appreciated, the data of Table I not only provides an extensive list of releasable marker substances of differing chemical composition, but also presents the preferred derivatizing agent to be employed with that releasable marker substance in the present invention. Details regarding the interaction of the marker substance with its preferred derivatizing agent are given below.

Means For Releasing The Marker Substance

As is illustrated in FIGS. 1–3, after the reaction products have been separated into individual fractions, the methodology relies upon the ability to release the marker substance from the conjugate reactant (bound or unbound) in the separated fraction. It is preferred that the means for achieving such release be as gentle as possible in order to prevent the marker substance from being substantively altered or adversely affected. The marker substance may be released from the conjugate reactant in any separated fraction using a variety of physical or chemical means including: acid-hydrolysis; heat; chelating agents; and enzymatic hydrolysis. The desired effect in each instance regardless of specific means employed is to destabilize the conjugate reactant, to cleave the existing imine bond, and to release the marker substance in a form having a functional carbonyl group again available for chemical reaction. For the marker substances listed in Table I, the preferred method for release is acid hydrolysis. This is accomplished by treating the individual fraction with an organic or metallic acid. In practice, the conjugate reactants (type 1 and type 2) wer found to be pH stable at neutral values. However, when the pH of the fluid is 2.0 or less hydrolysis of the conjugate reactant occurs immediately with concomitant release of the marker substance in a functionally intact form. It is most preferred that organic acids rather than metallic acids be utilized for this purpose; the range of useful acids includes acetic acid, maleic acid, lactic acid and the like. The useful metallic acids include sulfuric acid and hydrochloric acid respectively. In other instances, gentle heating of the individual fraction or the addition of an appropriate specific enzyme to the separated fraction will also yield the release of the marker substance in a useful fashion consistently.

Another mode for achieving the release of the marker substance from the bound or unbound conjugate reactant involves addition of strong chelating agents to the reaction products in the separated fractions. Such chelating agents compete for the metallic cation of the stabilized imine complex; in view of their high affinity for metal ions and the recognized stability of the chelate formed with such cations, these chelating agents are especially preferred as means for destabilizig the imine complex and causing release of the marker substance in a functional form. A representative list of useful chelating agents includes EDTA (ethylene diamine tetraacetic acid and its various derivatives and analogues; gluconic acid; kojic acid; oxalic acid; Quadrol [N,N,N',N'-bis (2-hydroxypropyl) ethylene diamine]; and citric acid.

A noteworthy feature concomitant with any of the chosen means for releasing the marker substance from an individual fraction is the ability of the chosen marker substance to readily vaporize in its released state from an aqueous system and to subsequently contact and react in vapor form with the derivatizing agent. The ability of a marker substance to vaporize upon release is especially useful when minimal volumes of fluid are employed in thin fluid streams which promote and enhance the vaporizing capacity of the marker substance upon release. Alternatively, if desired, means may be selected which induce the released marker substance to remain within the fluid and prevents its vaporization. Nevertheless, using the apparatus to be described hereinafter, it is preferred that the marker substance be released from any complexed conjugate reactant or unbound conjugate reactant fraction such that it vaporizes immediately upon release and is combined with the derivatizing agent while remaining in vapor form.

The Derivatizing Agent

The derivatizing agent is an amine containing chemical composition which is preferably immobilized onto the surface of a solid substrate. As such, it is able to combine with the released marker substance in the vaporized or fluid-dissolved state to form a reaction product in-situ which serves as a series of nucleating sites for subsequent formation and growth of crystals. It is preferred that the derivatizing agent be immobilized on the surface of the solid substrate as a substantially monodispersed system of particles having a size in the micron and submicron range. The use of such derivatizing agents as films of monodispersed particles in combination with supersaturated solutions for the detection, and identification of small crystals has been described in the literature [Vonnegut, B., *Science* 116:300–301 (1952); U.S. Pat. No. 4,380,587]. The immobilized derivatizing agent used in the present invention is thus a dispersion of particles substantially of the same size which is retained on the surface of a solid substrate with relatively uniform spacing between them, the particles preferably ranging about 0.1 μm–1.0 μm in size. A useful but not exhaustive listing of compositions useful as preferred derivatizing agents are given within Table I. It will be noted also that a single derivatizing agent may be used for reaction with a variety of different releasable marker substances, in vaporized or fluid dissolved states—each of which will then react with the chosen derivatizing agent to form a plurality of nucleating sites in-situ on the surface of the solid substrate. It will be understood that the nucleating sites formed in-situ are themselves crystals which are invisible to the unaided eye and which serve as specific initiation sites for the formation and growth of optically detectable crystals subsequently.

A film of monodispersed particles comprising the derivatizing agent is conveniently prepared by directing an aerosol of the solution of the derivatizing agent against the surface of a solid substrate in the conventionally known manner. By maintaining very accurate control over the concentration in the aerosol over time and controlling the speed of delivery of the aerosol to the surface of the solid, one may deposit an accurately controlled amount of the derivatizing agent onto the surface. To obtain satisfactory adherence of the aerosol particles to the surface of the solid, it is often desirable (but not necessary) to pretreat the surface by application of an electrostatic charge and/or heating the aerosol. Equipment for forming the aerosol in the desired size range of particles is commercially available.

It should be noted also that the solid substrate upon which the derivatizing agent is immobilized may be shaped into a variety of different forms and configurations. In this way, a variety of apparatus and articles may be prepared as test kits which employ the immobilized derivatizing agent in the described manner for reaction with the released marker substance and for formation of a plurality of nucleating sites in-situ. The variety of articles and apparatus useful for kit form will be described hereinafter.

The Metastable Supersaturated (Developer) Solution

The metastable supersaturated (developer) solution is an aqueous or non-aqueous fluid containing a supersaturated concentration of a crystal growing chemical composition which is chemically and physically stable for a defined period of time despite its supersaturated concentration. When combined with the nucleating sites on the surface of the solid substrate, crystallization will occur at each of the individual nucleating sites resulting in the formation and growth of optically detectable crystals. A useful but non-exhaustive list of preferred metastable supersaturated (developer) solutions is given in Table I, each developer solution being correlated with a preferred derivatizing agent and a releasable marker substance. The quantities of each chemical composition and the manner of utilizing each particular chemical composition to prepare a metastable supersaturated (developer) solution in aqueous and non-aqueous fluids are conventionally known in the art.

It is noteworthy that the listing of Table I indicates that the metastable supersaturated solution is almost always a supersaturated solution of a composition which is, in fact, the reaction product formed by the combination of the marker substance and the immobilized derivatizing agent. In the majority of instances, therefore, there is complete chemical identity between the composition of the nucleating sites formed in-situ and the chemical composition of the metastable supersaturated solution which crystallizes and deposits matter around each individual nucleating site during the crystallization process. In certain instances, the chemical composition of the metastable supersaturated solution is not chemically identical to the individual nucleating sites but is sufficiently similar to induce the crystallization process.

It is noteworthy that the nature and size of the crystals formed and grown on the surface of the solid substrate are directly affected by the number of nucleating sites initially formed in-situ by the interaction of the released marker substance and the immobilized derivatizing agent. Relatively speaking, if the separated fraction tested releases only a small quantity of marker substance, relatively few nucleating sites are formed on the surface of the solid; alternatively, if the individual separated fraction releases a relatively large quantity of marker substance, a proportionately larger number of individual nucleating sites will be formed on the surface of the solid. The number of nucleating sites formed directly determines the ultimate size of the crystals grown since the amount of crystallizable compound in the developer solution will be divided equally among all the nucelating sites regardless of their number. Accordingly, if a large number of nucleating sites are present the quantity of crystallizing compound in the developer solution is distributed over a greater number of nucleating sites and the size of each crystal formed and grown is relatively small. Conversely, if the number of nucleating sites formed is relatively small, the same concentration of crystallizable matter in the developer solution will be equally distributed over a smaller number of individual sites, thereby causing a greater quantity of material to be deposited on each site individually. This causes the formation and growth of larger sized crystals.

The true concentration of the crystallizable matter in the metastable supersaturated (developer) solution thus is important in that the concentration should be uniform and be of sufficient magnitude to provide for the growth of optically detectable crystals even when the number of individual nucleating sites is at a maximum. For this reason, metastable supersaturated (developer) solutions are preferably prepared at a concentration ranging from 2-10 times saturation. By using such developer solutions in uniform metastable concentrations, rapid crystal formation and growth usually occurs after one or two minutes contact with the individual nucleating sites. Typically, maximum crystal growth is obtained within 5-10 minutes and is visibly complete in all respects in not more than 60 minutes time. It is also expected and preferred that all other factors influencing the interaction between the metastable supersaturated (developer) solution and the nucleating sites on the surface of a solid substrate be controlled. In this way, the rate of matter deposition will be uniform in all respects.

The control of the speed of matter deposition also directly affects the ability of the grown crystals to be optically detected. For example, a rapid deposition of crystallizable material from the developer solution onto the nucleating sites tends to build up the crystal face towards an irregular point; whereas more leisurely deposition of crystallizable material produces a crystalline lattice whose crystal face is essentially flat. Optically, light is scattered more readily from crystals which have irregular and pointed faces and thus become more "visible" as a result of the light scattering effect; in comparison, flat-faced crystal lattices scatter light minimally and are more difficult to visualize with the unaided eye or with the use of specific detection equipment. For this reason also, it is preferred that, in all instances, the concentration of chemical compositions used in making metastable supersaturated (developer) solutions be as concentrated as possible in order to promote rapid deposition of the crystalline material when brought into reactive contact with the individual nucleating sites.

In addition, because of the inherent instability of a supersaturated solution prepared in maximum concentration, it is advisable to prepare the developer solution just prior to use. Furthermore, stabilizers such as polyvinyl alcohol, polyvinylpyrrolidone, gelatin, agar, sodium carboxymethyl cellulose, methyl and ethyl cellulose and the like are useful and desirable for prolonging the effective life of the supersaturated developer solution in the present invention. As a practical matter therefore, it is convenient to have two prepared reagents available, one or both of which is in solution, which may be mixed at a predetermined ratio on-site to form the metastable supersaturated (developer) solution. The mixed solution may be then combined with the nucleating sites on the surface of the solid substrate.

The effect of forming and growing crystals gives rise to an optically observable and detectable change which is a measure of the analyte of interest in the fluid test sample. The degree of optically detectable crystals provides both a qualitative and/or quantitative measure of the reactants in any separated fraction, which in turn, is correlatable with a calculated amount of analyte of interest in the fluid sample. Typically, quantitative results in the nanogram per milliliter range may be reproducibly obtained by the formation and growth of optically detectable crystals in the described manner. For best quantitative results, it is preferred that a single optical measurement such as diffuse reflection be utilized as an indirect correlation for calculating the quantity of analyte of interest in the test sample.

ILLUSTRATIVE EXAMPLE

To illustrate the detection methods which utilize the chemical components described earlier herein, the immunodiagnostic assay of human chorionic gonadotropin (hereinafter "hCG") will be described in detail. It will be appreciated that the determination quantitatively of hCG in urine samples from human female persons is utilized routinely as a test for pregnancy. However, it will be expressly understood that this example is solely illustrative and not limiting of either the applications or the scope of the present invention.

Manufacture of Reactants

The methodology is utilized in a competitive binding assay protocol in which hCG is the analyte of interest; commercially available hCG bound to red blood cells using methods available in the prior art literature [Kabat and Mayer, *Experimental Immunochemistry* (Second Edition), Charles C. Thomas, Springfield, Ill., 1971, pg. 120] is the ligand analogue; and the conjugate reactant comprises anti-human chorionic gonadotropin antibody (the specific binding partner), cupric acetate (the chelatable metallic cation), and salicylaldehyde (the releasable marker substance).

The type 1 conjugate reactant was prepared as follows: the salicylaldehyde reagent was made by dissolving 0.1 ml salicylaldehyde (Aldrich Chemical Company) in 80 ml of distilled water with mixing. To the solution was added 50 mg of sodium acetate (Fisher Scientific Company) to form a resulting fluid reagent having a pH of 6.6 and which is yellow in color. To 1.0 ml of this salicylaldehyde reagent was added 1.0 ml of anti-human chorionic gonadatropin antibody raised in rabbits (rabbit anti-hCG=6.5 mg/ml by globulin assay). This fluid mixture was allowed to react at 3° C. for 3 days' duration. Subsequently, the reaction mixture was brought to room temperature and 1.0 ml of 0.2% cupric actate solution (pH 5.9) was added to the fluid. The resulting solution had a slight turbidity, was yellow in color, and had a pH of 5.7. This resulting solution was then allowed to stand for one hour during which a yellow precipitate was formed. The solution was then centrifuged, typically at 10,000× gravity for 30 minutes, and the supernatant removed. This supernatant fraction contained the copper stabilized salicylidene-/anti-human chorionic gonadotropin imine complex which was then purified in the following manner.

To 2.2 ml of the supernatant was added 1.1 ml of 8% TRIS [tris-(hydroxymethyl)-aminomethane, ICN Nutritional Biochemicals Company]. This fluid mixture was then purified using a 4 cubic centimeter Sephacryl S-200 column (Pharmacia Corporation) using a 0.1M TRIS buffer, pH 7.4, containing 0.001M $CuCl_2$ (Mallinckrodt Chemical Company) as the eluant. During eluation, a series of 0.5 ml fluid fractions were collected and those fractions demonstrating an ultraviolet absorption at 280 nanometers were identified as containing the desired protein fraction. A yield of 69% based on protein was obtained. The purified conjugate reactant obtained in this manner was found to contain 4 molecules of salicylaldehyde per molecule of rabbit anti-human chorionic gonadotropin upon analysis.

The immobilized derivatizing agent was prepared as follows: 2.5 grams of gold label grade semicarbazide hydrochloride (Aldrich Chemical Company) and 2.5 grams of ammonium oxalate (Mallinckrodt Chemical Company) were dissolved in 10 ml of distilled water. This solution was then added with stirring to 240 ml of methanol to yield a fluid having a pH of 3.7. This semicarbazide hydrochloride solution was applied to a 5 ml fluorinated polyethylene/polypropylene polymer, the solid substrate. The semicarbazide hydrochloride solution was preferrably applied using a fluid atomization aerosol generator (Environmental Research Corporation) set at: air pressure=38; atomization=90; dilution=60; and an aerosol delivery tube which was 45" long, 1" in diameter, and contained a 3×0.25" opening. The aerosol was heated to 110° C. during the coating process. The speed of delivery for the aerosol typically ranged between about 6" per minute and 15" per minute. The semicarbazide hydrochloride particles serving as the immobilized derivatizing agent on the surface of this solid substrate ranged from about 0.4 um to about 0.6 um in size.

The metastable supersaturated (developer) solution was prepared as follows: to avoid instability, the developer solution was prepared by mixing two different fluids immediately before use to form the supersaturated developer solution. Fluid A was made by adding 0.2 ml of salicylaldehyde (Aldrich Chemical Company) to 10 grams of water-soluble gelatin (Kind and Knox Company) in 10 ml of distilled water. Fluid B was made by dissolving 0.15 grams of semicarbazide hydrochloride (Aldrich Chemical Company) in 100 ml of distilled water. The fluids A and B respectively remain stable for an extended period of time. When the metastable supersaturated (developer) solution is required in use, equal quantities of fluid A and fluid B are combined to immediately yield a useful developer solution comprising salicylaldene semicarbazone. The developer solution is used promptly after its formation.

Illustrative Protocol

The preferred protocol for performing the competitive binding assay is as follows:

1. The following ingredients are added to a test tube:
   100–200 ul of type 1 conjugate reactant;
   100–200 ul of 0.15M borate phosphate buffer pH 6.0;
   100–200 ul of fluid test sample, typically urine believed to contain hCG;
   350–600 ul of a 0.5% suspension of stabilized sheep red blood cells previously reacted with hCG in the earlier described manner.

2. This reaction mixture was gently mixed and allowed to stand undisturbed for between 1 and 2 hour's duration at room temperature.

3. At the end of this reaction period, the reaction mixture was evaluated to determine whether agglutination had occurred; accordingly, the reaction mixture was then centrifuged at 2000× gravity for approximately 10 minutes' duration.

4. The supernatant was removed and transferred to a clean test tube containing about 100 milligrams of citric acid; this fluid mixture was then gently mixed by hand.

5. The derivatizing agent previously immobilized onto the solid substrate is then combined with the fluid of the test tube and the top of the test tube sealed with parafilm. The sealing with parafilm will prevent the vaporized marker substance, the released salicylaldehyde, from being dissipated.

6. After between 5–30 minutes incubation at room temperature, the solid substrate was removed and then immersed in the freshly prepared metastable supersaturated (developer) solution in a volume sufficient to cover the surface of the solid substrate. This immersion continued for 5–10 minutes duration.

7. The solid substrate was removed from the developer solution and a film of optically detectable crystals visible to the unaided eye was observed. The presence of the formed crystals qualitatively indicates the existence of hCG in the urine sample; measurement of the opacity of the crystallized film on the surface of solid substrate is correlatable to predetermined, standardized quantities of hCG and thus provides quantitative results if desired.

TEST KITS UTILIZING THE NOVEL DETECTION METHODOLOGY

It is expected and intended that a variety of test kits may be prepared in advance for the detection of one or more analytes of interest believed to be present in a fluid sample. It will be understood that the fluid sample may be obtained from any source (human, animal, drinking water, etc.) and may in fact be a manufactured fluid preparation in which the desired analyte has been solubilized or immobilized onto an inert carrier for purposes of qualitative and/or quantitative detection. So long as the analyte of interest to be detected meets the criteria of being dissolved, suspended, or supported by an inert carrier, the true chemical composition and/or structural organization of the analyte is irrelevant.

Test kits for detecting an analyte of interest in a fluid sample would thus comprise the following: a conjugate reactant comprising (a) a binding partner specific for the analyte of interest, the binding partner having at least one amine group available for reaction, (b) a chelatable metallic cation, and (c) a releasable marker substance having at least one carbonyl group available for reaction; means for combining the fluid sample with the conjugate reactant as a reaction mixture; means for separating the products of the reaction mixture into individual fractions; means for releasing the marker substance from the bound and unbound conjugate reactant; an immobilized derivatizing agent able to combine with the released marker substance such that a plurality of nucleating sites are formed in-situ, the derivatizing agent being immobilized onto the surface of a solid substrate; and a metastable supersaturated (developer) solution which preferably is prepared on site at the time of assay.

Figure 4:
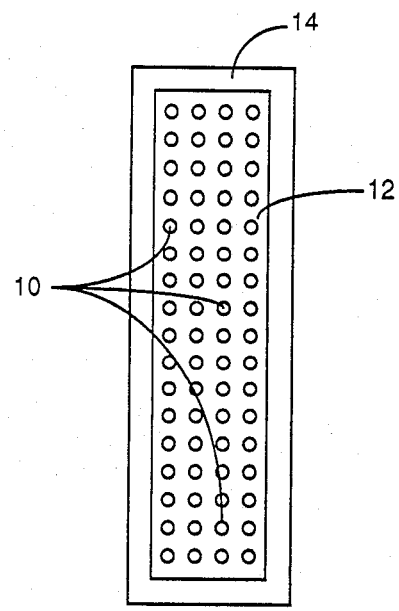
FIG. 4 is an illustration of one embodiment of the derivatizing agent immobilized onto the surface of a solid phase substrate.
Figure 5:
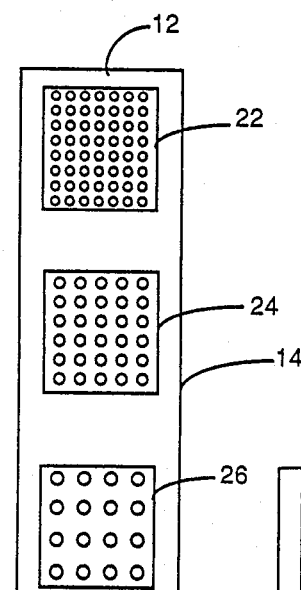
FIG. 5 is an illustration of a preferred embodiment for the derivatizing agent immobilized onto the surface of a solid substrate in discrete block zones.
Figure 6:
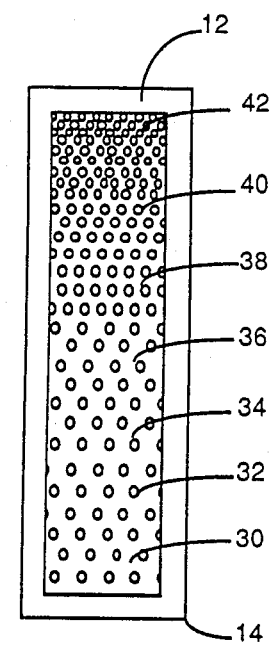
FIG. 6 is an illustration of a preferred embodiment for the derivatizing agent immobilized onto the surface of a solid substrate as a density gradient.

In the kit apparatus described above, the derivatizing agent immobilized onto the surface of a solid substrate may take the form of a dipstick based on the concept described in the illustrative example to detect hCG. Such dipsticks are illustrated by FIGS. 4, 5, and 6 respectively. The major differences between each of these embodiments is the concentration of derivatizing agent employed and the distribution of the derivatizing agent as a function of the number of particles per square unit of area. Accordingly, as seen in FIG. 4, the derivatizing agent is distributed as uniformly dispersed particles 10 over the entirety of the surface 12 of the solid substrate 14; although the precise dimensions may be varied to meet the user's needs or convenience, the critical feature is that the dispersion be uniform over the entirety of the surface area. As a result, when the released marker substance comes in contact with the particles 10 of derivatizing agent, a uniform series of nucleating sites is formed in-situ, the concentration and density of which will be consistent over the surface 12 of the solid 14.

Alternative Embodiments

In the alternative, the embodiments of FIGS. 5 and 6 provide quantitative data regarding the concentration of the analyte of interest in the fluid sample. In these embodiments, the derivatizing agent 10 is applied in discrete blocks 22, 24, and 26 respectively, each of which contains ever-increasing concentrations of derivatizing agent within identical surface areas. The embodiment illustrated by FIG. 5 illustrates increasing concentrations of immobilized derivatizing agent as a series of discrete blocks; in comparison, the embodiment of FIG. 6 provides a continuously changing density gradient of immobilized derivatizing agent - in which the concentration in zone 30 is quantitatively the least, followed by zones of ever-increasing concentrations 32, 34, 36, 38, and 40 until the maximum density and concentration of derivatizing agent is obtained in zone 42. When a released marker substance comes in contact with the immobilized derivatizing agent in these zones, the plurality of nucleating sites will be formed in the direction of increasing density of derivatizing agent. Accordingly, the more marker substance that is released, the greater the density of derivatizing agent that will chemically react to form nucleating sites in-situ. When all of the released marker substance has been completely reacted and exhausted, that portion of the immobilized derivatizing agent which was more dense than required will be superfluous. As a result, when the developer solution is added, crystallization will occur only in those zones where nucleating sites have been formed. In this manner, the greater the amount of marker substance released, the larger the zones of derivatizing agent reacted and the greater the surface area of crystallization.

Preferred Kits

Figure 7A:
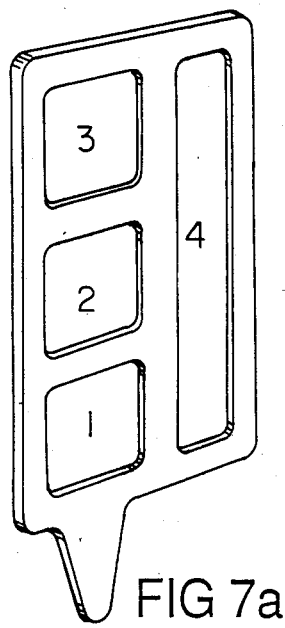
FIGS. 7a-7e illustrate a preferred test kit for performing the methods of the present invention.
Figure 7B:
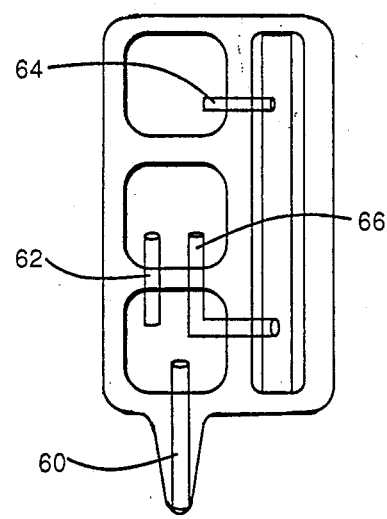
Figure 7C:
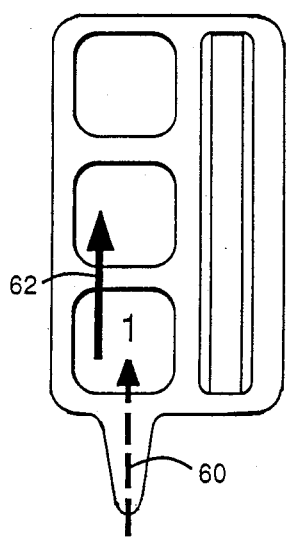
Figure 7D:
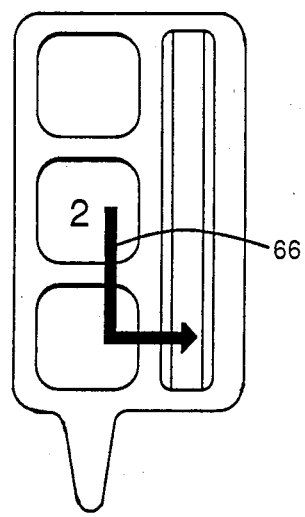
Figure 7E:
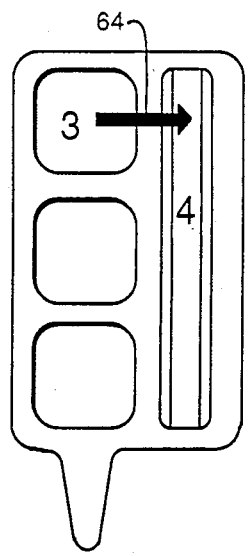

The preferred kit for practicing the methodology of the present invention is illustrated by FIGS. 7a -7e respectively. As seen in FIG. 7a, a kit in the form of a prepared article having four distinct chambers is provided to the user. The individual chambers 1, 2, 3, and 4, respectively have limited access to one another as illustrated in FIG. 7b. Accordingly, chamber 1 provides access for the introduction of a fluid sample via conduit 60. An exit pathway 62 allows fluid from chamber 1 to flow into the interior of chamber 2. Similarly, an exit pathway 66 allows fluid or vapor within chamber 2 to flow directly without interruption into one end of chamber 4. Lastly, a flow pathway 64 allows fluid from chamber 3 to be introduced into the other end of chamber 4 as well.

It is intended that each of the respective chambers 1, 2, 3, and 4 be used in the following manner. The test kit as a whole is specifically prepared for the detection of a particular analyte of interest such as hCG. Chamber 1 has immobilized onto its interior surfaces the ligand analogue—in this instance, a known limited concentration of hCG molecules. In addition, chamber 1 contains the conjugate reactant in a dried form, the conjugate reactant comprising a specific binding partner for hCG, a chelatable metallic cation, and a releasable marker substance prepared as previously described in the illustrative example. Chamber 2 contains the means for releasing the marker substance in a prepared dry state; a preferred example of the releasing means would be a limited concentration of citric acid as a dried or lyophilized powder. Chamber 3 contains the metastable supersaturated (developer) solution of choice which is preferably introduced into chamber 3 only at the time of test. Chamber 4 in fact is a miniature embodiment of the dipstick previously illustrated in FIGS. 4, 5 and 6 which contains a known quantity of an immobilized derivatizing agent. The sequence of manipulative steps comprising the present invention is then indicated by the arrows in FIGS. 7c, 7d, and 7e respectively. The test fluid suspected of containing the analyte of interest hCG is introduced through the conduit 60 into chamber 1 thereby solubilizing the conjugate reactant contained therein. A competitive binding reaction occurs within chamber 1 which is allowed to continue for a predetermined period of time. The competitive binding reactions previously described herein all occur within the interior of chamber 1. After the designated reaction time has elapsed, the reaction fluid is physically squeezed out through the flow pathway 62 into the interior of chamber 2 which contains citric acid, the means for releasing the marker substance. In this mode, such marker substance as is released by the citric acid in chamber 2 is vaporized and carried via the flow pathway 66 into one end of chamber 4. The transfer of the released marker substance in vapor form is allowed to occur for a predetermined length of time, typically a few minutes. This results in the formation of nucleating sites within chamber 4. Subsequently, the metastable supersaturated (developer) solution is introduced into chamber 3 and in turn physically squeezed through the flow path 64 to enter chamber 4 at it's other end. The developer solution is allowed to flow over the entirety of the surface area of chamber 4 and will initiate formation of crystals on the nucleating sites previously formed by the reaction of the immobilized derivatizing agent with the vaporized marker substance. After approximately 10 minutes' duration, the excess developer solution is removed from chamber 4.

The presence of formed grown crystals is detectable by the unaided eye after 5-10 minutes. The presence of optically detectable crystals is a qualitative measure that some hCG was present in the fluid test sample; the opacity of the grown crystals as it extends upward within chamber 4 provides a quantitative measure of the amount of hCG present in the test fluid.

The present invention is not to be limited in form nor restricted in scope except by the claims appended hereto.

What we claim is:

1. A method for detecting an analyte of interest in a fluid sample comprising the steps of:
   obtaining a conjugate reactant comprising
   (a) a binding partner specific for the analyte of interest, said binding partner having at least one amine group available for reaction,
   (b) a metallic cation,
   (c) a releasable marker substance having at least one carbonyl group available for reaction,
   wherein said specific binding partner and said metallic cation and said releasable marker substance have combined to form the conjugate reactant;
   combining the fluid sample with said conjugate reactant such that the analyte of interest binds to at least a portion of said conjugate reactant to form an analyte complexed product;
   separating said analyte complexed product from the unbound portion of said conjugate reactant as inidividual fractions;
   releasing said marker substance from at least one of the separated individual fractions selected from the group consisting of said analyte complexed product fraction and said unbound conjugate reactant fraction;
   combining said released marker substance with an immobilized derivatizing agent such that a plurality of nucleating sites are formed in situ, said derivatizing agent being immobilized onto the surface of solid substrate;
   treating said nucleating sites with a metastable supersaturated solution such that a plurality of optically detectable crystals are formed; and
   optically detecting the presence of said formed crystals, said crystals being a measure of the analyte of interest in the fluid sample.

2. A method for detecting an analyte of interest in a fluid sample comprising the steps of:
   obtaining a ligand analogue, that is a ligand analogous to the analyte of interest;
   obtaining a conjugate reactant comprising
   (a) a binding partner specific for the analyte of interest and said ligand analogue, said binding partner having at least one amine group available for reaction,
   (b) a metallic cation,
   (c) a releasable marker substance having at least one carbonyl group available for a reaction,
   wherein said specific binding partner and said metallic cation and said releasable marker substance have combined to form the conjugate reactant;
   combining the fluid sample with said conjugate reactant such that the analyte of interest binds to at least a portion of said conjugate reactant to form an analyte complexed product and the remainder of said conjugate reactant remains unbound;
   adding said ligand analogue to the fluid sample such that said ligand analogue binds to such unbound conjugate reactant as is present in the fluid to form a ligand analogue complexed product;
   separating said analyte complexed product from said ligand analogue complexed product as individual fractions;
   releasing said marker substance from at least one of the separated individual fractions selected from the group consisting of said analyte complexed product fraction and said ligand analogue complexed product fraction;
   combining said released marker substance with an immobilized derivatizing agent such that a plurality of nucleating sites are formed in situ, said derivatizing agent being immobilized onto the surface of a solid substrate;
   treating said nucleating sites with a metastable supersaturated solution such that a plurality of optically detectable crystals are formed; and
   optically detecting the presence of said formed crystals, said formed crystals being a measure of the analyte of interest in the fluid sample.

3. A methods for detecting an analyte of interest in a fluid sample comprising the steps of:
   obtaining a conjugate reactant comprising
   (a) a ligand analogue, that is a ligand analogous to the analyte of interest, said ligand analogue having at least one amine group available for reaction,
   (b) a metallic cation,
   (c) a releasable marker substance having at least one carbonyl group available for reaction,
   wherein said ligand analogue and said metallic cation and said releasable marker substance have combined to form a conjugate;
   obtaining a binding partner for said ligand analogue and for the analyte of interest;
   combining the fluid sample with said specific binding partner such that at least a portion of the analyte of interest binds to said specific binding partner to form a bound analyte product and the remainder of said specific binding partner remains unbound;
   adding said conjugate reactant to said fluid sample such that the unbound portion of said specific binding partner binds to at least a portion of said conjugate reactant to form a ligand analogue complexed product wherein the remainder of said conjugate reactant remains unbound;

separating said ligand analogue complexed product from said unbound conjugate reactant as individual fractions;

releasing said marker substance from at least one of the separated individual fractions selected from the group consisting of said ligand analogue complexed product fraction and said unbound conjugate reactant fraction;

combining said released marker substance with an immobilized derivatizing agent such that a plurality of nucleating sites are formed in situ, said derivatizing agent being immobilized onto the surface of a solid substrate;

treating said nucleating sites with a metastable supersaturated solution such that a plurality of optically detectable crystals are formed; and optically detecting the presence of said formed crystals, said formed crystals being a measure of the analyte of interest in the fluid sample.

4. The detection method as recited in claim 2 wherein said ligand analogue is added to the fluid sample simultaneously with said conjugate reactant.

5. The detection method as recited in claim 3 wherein said specific binding partner is added to the reaction mixture simultaneously with said conjugate reaction.

6. The detection method as recited in claim 1, 2, or 3 wherein said crystal detection is a qualitative measure of the analyte of interest.

7. The detection method as recited in claim 1, 2, or 3 wherein said crystal detection is a quantitative measure of the analyte of interest.

8. The detection method as recited in claim 1, 2, or 3 wherein said ligand analogue is a composition selected from the group consisting of amino acids, polypeptides, proteins, and their derivatives.

9. The detection method as recited in claim 1, 2, or 3 wherein said specific binding partner is a composition selected from the group consisting of polypeptides, proteins, and their respective derivatives.

10. The detection method as recited in claim 1, 2, or 3 wherein said ligand analogue is selected from the group consisting of antigens, haptens, enzymes, antibodies, antibody fragments, enzyme substrates and enzyme co-factors.

11. The detection method as recited in claim 1, 2, or 3 wherein said specific binding partner is selected from the group consisting of antigens, haptens, antibodies, antibody fragments, enzymes, enzyme substrates, and enzymatic co-factors.

12. The detection method as recited in claim 1, 2, or 3 wherein said releasable marker substance is selected from the group consisting of alkyl compounds, aryl compounds, aromatic compounds, and aliphatic compounds.

13. The detection method as recited in claim 1, 2, or 3 wherein said releasable marker substance is selected from the group consisting of Salicylaldehyde, 4-Chloro-salicylaldehyde, 5-Chloro-salicylaldehyde, 4,6-Dimethylsalicylaldehyde, 3-Ethoxyl-salicylaldehyde, 3-Fluorosalicylaldehyde, 4-Methoxy-salicylaldehyde, 5-Methyl-salicylaldehyde, 5-Sulfo-salicylaldehyde, 2-Hydroxy-1-naphthaldehyde, 2-Hydroxy-3-naphthaldehyde, 2-Hydroxy Cinnamaldehyde, Pyridoxal, 2-Thiophene Aldehyde, Pyrrolaldehyde, 4-Hydroxynicotinaldehyde, and 3-Hydroxy Isonicotinaldehyde.

14. The detection method as recited in claim 1, 2, or 3 wherein said immobilized derivatizing agent is a composition able to form an imine with said released marker substance.

15. The detection method as recited in claim 1, 2, or 3 wherein said derivatizing agent is selected from the group consisting of p-Hydroxybenzoic Acid Hydrazide, Salicylhydrazide, Nicotinic Acid Hydrazide, 2,4-Dinitrophenyl Hydrazine, p-Carboxyphenyl Hydrazine, and Semicarbazide.

16. The detection method as recited in claim 1, 2, or 3 wherein said metastable supersaturated solution is a composition identical to the reaction product of said released marker substance and said derivatizing agent.

17. The detection method as recited in claim 1, 2, or 3 wherein said metastable supersaturated solution is selected from the group consisting of Salicylaldehyde-p-Hydroxybenzoic Acid Hydrazone, 4-Chloro-salicylaldehyde-p-Hydroxybenzoic Acid Hydrazone (Salicylaldehyde-p-Hydroxybenzoic Acid Hydrazone, 5-Chloro-salicylaldehyde-p-Hydroxybenzoic Acid Hydrazone, 4,6-Dimethyl-salicylaldehyde Salicylhydrazone, 3-Ethoxy-salicylaldehyde Salicylhydrazone, 3-Fluoro-salicylaldehyde Salicylhydrazone, 4-Methoxy-salicylaldehyde Nicotinic Acid Hydrazone, 5-Methyl-salicylaldehyde Nicotinic Acid Hydrazone, 5-Sulfo-salicylaldehyde Nicotinic Acid Hydrazone, 2-Hydroxy-1-naphthaldehyde 2,4-Dinitrophenyl Hydrazone, 2-Hydroxy-3-naphthaldehyde 2,4-Dinitrophenyl Hydrazone, 2-Hydroxy Cinnamaldehyde-p-Carboxyphenyl Hydrazone, Pyridoxal-p-Carboxylphenyl Hydrazone, 2-Thiophene-aldehyde-p-Carboxyphenyl Hydrazone, Pyrrolaldehyde-Semicarbazone, 4-Hydroxynicotinaldehyde-Semicarbazone, and 3-Hydroxy Isonicotinaldehyde-Semicarbazone.

18. The detection method as recited in claim 1, 2, or 3 wherein said release of said marker substance is achieved via a lowering of pH.

19. The detection method as recited in claim 1, 2, or 3 wherein said release of said marker substance is achieved via addition of heat.

20. The detection method as recited in claim 1, 2, or 3 wherein said release of said marker substance is achieved via addition of a chelating agent.

21. The detection method as recited in claim 1, 2, or 3 wherein said release of said marker substance is achieved via enzymatic hydrolysis.

22. The detection method as recited in claim 18 wherein said reduction of pH occurs by the addition of acid.

23. The detection method as recited in claim 22 wherein said acid is selected from the group consisting of organic acids and metallic acids.

24. The detection method as recited in claim 1, 2, or 3 wherein said method is an immunodiagnostic assay.

25. The detection method as recited in claim 1, 2, or 3 wherein said method is an environmental assay.

26. The detection method as recited in claim 1, 2, or 3 wherein said method is an analytical biochemical assay.

27. A test kit for detecting an analyte of interest in a fluid sample comprising: a conjugate reactant comprising (a) a binding partner specific for the analyte of interest and a ligand analogous to the analyte of interest, said binding partner having at least one amine group available for reaction,
(b) a metallic cation,
(c) a releasable marker substance having at least one carbonyl group available for a reaction,
wherein said specific binding partner and said metallic cation and said releasable marker substance have combined to form the conjugate reactant;
means for combining said fluid sample and said conjugate reactant such that at least a portion of said conjugated reactant to the analyte of interest and the remaining portion of said conjugate reactant remains unbound;
means for separating said bound conjugate reactant and said unbound conjugate reactant into separate fractions;
means for releasing said marker substance from at least one of said separated fractions selected from the group consisting of said bound conjugated reactant fraction and said unbound conjugated reactant fraction;
an immobilized derivatizing agent for a combination with a released marker substance such that a plurality of nucleating sites are formed in situ, said derivatizing agent being immobilized onto the surface of solid substrate; and
a metastable supersaturated solution for treating said formed nucleating sites such that a plurality of optically detectable crystals are formed, the presence of said detectable crystals being a measure of the analyte of interest in the fluid sample.

28. The test as recited in 27 further comprising a ligand analogue, that is a ligand analogous to the analyte of interest.

29. A test kit for detecting an analyte of interest in a fluid sample comprising:
a conjugate reactant comprising
(a) a ligand analogue, that is a ligand analogous to the analyte of interest, said ligand analogue having at least one amine group available for a reaction,
(b) a metallic cation,
(c) a releasable marker substance having at least one carbonyl group available for reaction,
wherein said ligand analogue and said metallic cation and said releasable marker substance have combined to form a conjugate;
a binding partner specific for said ligand analogue and specific for the analyte of interest;
means for combining said fluid sample and said conjugated reactant and said specific binding partner as a reaction mixture such that at least a portion of said specific binding partner binds to said conjugate reactant to form a ligand analogue complexed product and a portion of said conjugated reactant remains unbound;
means for spearating said ligand analogue complexed product and said unbound conjugated reactant into separate fractions;
means for releasing said marker substance from at least one of the separated fractions selected from the group consisting of the ligand analogue complexed product fraction and said unbound conjugate reactant fraction;
an immobilized derivatizing agent able to combine with said released marker substance such that a plurality of nucleating sites are formed in situ, said derivatizing agent being immobilized onto the surface of a solid substrate; and
a metastable supersaturated solution for treating said formed nucleating sites such that a plurality of optically detectable crystals are formed, the presence of said detectable crystals being a measure of the anslyte of interest in the fluid sample.

* * * * *